United States Patent [19]

Zuzich et al.

[11] Patent Number: 5,428,178

[45] Date of Patent: Jun. 27, 1995

[54] POLYETHERCYCLIPOLYOLS FROM EPIHALOHYDRINS, POLYHYDRIC ALCOHOLS, AND METAL HYDROXIDES OR EPOXY ALCOHOLS AND OPTIONALLY POLYHYDRIC ALCOHOLS WITH THERMAL CONDENSATION

[75] Inventors: Anne H. Zuzich; George C. Blytas; Harry Frank, all of Houston, Tex.

[73] Assignee: Shell Oil Company, Houston, Tex.

[21] Appl. No.: 224,387

[22] Filed: Apr. 7, 1994

Related U.S. Application Data

[62] Division of Ser. No. 960,159, Oct. 13, 1992, abandoned.

[51] Int. Cl.⁶ .......................................... C07D 319/12
[52] U.S. Cl. ..................................................... 549/378
[58] Field of Search .......................................... 549/378

[56] References Cited

U.S. PATENT DOCUMENTS

| | | |
|---|---|---|
| 2,487,208 | 11/1949 | Alsop . |
| 3,425,960 | 2/1969 | Sandler et al. . |
| 3,548,010 | 12/1970 | Yoshino et al. . |
| 3,637,774 | 1/1972 | Babayan/Lehman . |
| 3,968,169 | 7/1976 | Seiden . |
| 4,802,998 | 2/1989 | Mueller et al. . |
| 5,058,679 | 11/1991 | Hale et al. . |
| 5,072,794 | 12/1991 | Hale et al. . |
| 5,076,364 | 12/1991 | Hale et al. . |
| 5,076,373 | 12/1991 | Hale et al. . |
| 5,083,622 | 1/1992 | Hale et al. . |
| 5,085,282 | 2/1992 | Hale et al. . |
| 5,198,416 | 3/1993 | Hale et al. . |
| 5,198,532 | 3/1993 | Blytas et al. . |
| 5,204,444 | 4/1993 | Frank et al. . |
| 5,233,055 | 8/1993 | Blytas et al. . |

FOREIGN PATENT DOCUMENTS

| | | |
|---|---|---|
| 324887A | 1/1988 | European Pat. Off. . |
| 374671A | 12/1988 | European Pat. Off. . |
| 374672A | 12/1988 | European Pat. Off. . |
| 382070A | 2/1989 | European Pat. Off. . |
| 382071A | 2/1989 | European Pat. Off. . |
| 386636A | 3/1989 | European Pat. Off. . |
| 386638A | 3/1989 | European Pat. Off. . |
| 391251A | 4/1989 | European Pat. Off. . |
| 391252A | 4/1989 | European Pat. Off. . |
| 398112A | 5/1989 | European Pat. Off. . |
| 399270A1 | 5/1989 | European Pat. Off. . |
| 333984A | 9/1989 | European Pat. Off. . |
| 3346097A | 12/1983 | Germany . |
| 3842692A | 6/1990 | Germany . |
| 7021948R | 6/1965 | Japan . |
| 1902868 | 4/1968 | Japan . |
| 44-26672 | 11/1969 | Japan . |
| 58-198429A | 5/1982 | Japan . |
| 61-043627A | 8/1984 | Japan . |
| 61-140534A | 12/1984 | Japan . |
| 61-238749A | 4/1985 | Japan . |
| 2216573A | 10/1989 | United Kingdom . |
| 2216574A | 10/1989 | United Kingdom . |
| 2223255A | 4/1990 | United Kingdom . |

*Primary Examiner*—James H. Reamer

[57] ABSTRACT

Method for preparing polyethercyclicpolyol by heating alkali and/or alkaline earth hydroxide optionally with polyol, its precursors or derivatives, admixing epoxy alcohol or epihalohydrin therewith to initiate an addition reaction, and thermally condensing the product of the addition reaction.

2 Claims, 5 Drawing Sheets

POLYETHERCYCLIPOLYOLS FROM EPIHALOHYDRINS, POLYHYDRIC ALCOHOLS, AND METAL HYDROXIDES OR EPOXY ALCOHOLS AND OPTIONALLY POLYHYDRIC ALCOHOLS WITH THERMAL CONDENSATION

This is a division of application Ser. No. 960,159 filed Oct. 13, 1992 now abandoned.

BACKGROUND OF THE INVENTION

1. Field of the Invention

This invention relates to polyethercyclicpolyols having high molecular weights and to the preparation thereof. In particular, the invention relates to the preparation of polyethercyclicpolyols which, due to improved molecular properties and characteristics, permit the preparation of improved drilling fluids.

2. Description of the Prior Art

Water-based drilling fluids of the prior art comprise water, clays or polymers, and various drilling fluid additives which control the physical, chemical and/or theological properties of drilling fluids in wellbores. It is desirable that such drilling fluid additives inhibit formation of gas hydrates, prevent shale dispersion, reduce swelling of the formation to improve wellbore stability, reduce fluid loss, and reduce filter cake thickness. In order to perform these functions as drilling fluid additives, it is theorized, although the present invention is not limited to this theory, that an ideal polymeric drilling fluid additive would contain large water soluble molecules and have relatively limited crosslinking in spite of high molecular weight. It is difficult to produce polymeric molecules of this type of high molecular weight which do not have extensive crosslinking, and the prior art has been unsuccessful in producing such an ideal drilling fluid additive which performs the desired functions. Accordingly, the present invention provides a process which overcomes these and other problems in the art as more particularly disclosed hereinafter, and which produces polyethercyclicpolyols of significantly improved characteristics as drilling fluid additives.

SUMMARY OF THE INVENTION

The purpose of the present invention is to form polyethercyclicpolyols by an addition reaction between an epihalohydrin and a polyol or by an addition reaction of an epoxy alcohol with itself and optionally with a polyol, followed by a thermal condensation reaction. This purpose is achieved by reacting an epihalohydrin, an alkali and/or alkaline earth metal hydroxide, and a reactant selected from the group consisting of (a) a polyol having at least two hydroxyl groups, (b) precursors of the polyol, (c) cyclic derivatives of the polyol, and (d) mixtures thereof, wherein the said polyol reactant and the metal hydroxide are first mixed and heated, the epihalohydrin is added to the mixture, heating of the mixture is continued until the addition reaction is complete, optionally adding additional polyol reactant to the mixture, further heating the mixture to initiate thermal condensation, removing water formed during the thermal condensation, optionally adding a final quantity of additional polyol reactant when the thermal condensation is within a preselected degree of completion, and continuing the thermal condensation to completion without undergoing degeneration. In another embodiment, the polyol reactant and the metal hydroxide are first mixed with a solvent and heated, the epihalohydrin is added to the mixture, heating of the mixture is continued until reaction is complete, optionally adding additional polyol reactant to the mixture, further heating the mixture to initiate thermal condensation, removing water formed during the thermal condensation, optionally adding a final quantity of additional polyol reactant when the thermal condensation is within a preselected degree of completion, and continuing the thermal condensation to completion without undergoing degeneration. In yet another embodiment of the invention, the polyol reactant and the metal hydroxide are first mixed and heated, the epihalohydrin is added to the mixture, water is removed from the mixture, heating of the mixture is continued until the reaction is complete, optionally adding additional polyol reactant to the mixture, further heating the mixture to initiate thermal condensation, removing water formed during the thermal condensation, optionally adding a final quantity of additional polyol reactant when the thermal condensation is within a preselected degree of completion, and continuing the thermal condensation to completion without undergoing degeneration. In an additional embodiment of the invention, the polyol reactant and the metal hydroxide are first mixed and heated and water is removed from the mixture, the epihalohydrin is added to the mixture, heating of the mixture is continued until the reaction is complete, optionally adding additional polyol reactant to the mixture, further heating the mixture to initiate thermal condensation, removing water formed during the thermal condensation, optionally adding a final quantity of additional polyol reactant when the thermal condensation is within a preselected degree of completion, and continuing the thermal condensation to completion without undergoing degeneration. In still another embodiment of the invention, the polyol reactant and the metal hydroxide are first mixed and heated, the epihalohydrin is added to the mixture, heating of the mixture is continued until the reaction is complete, optionally adding additional polyol reactant to the mixture, further heating the mixture to initiate thermal condensation, removing water formed during the thermal condensation, optionally adding a final quantity of additional polyol reactant when the thermal condensation is within a preselected degree of completion, and continuing the thermal condensation to completion without undergoing degeneration, after which an alkali and/or alkaline earth metal halide salt by product is removed from the mixture by the addition of a lower alkanol to the mixture to precipitate salt, followed by filtration or centrifugation of the mixture. In yet another embodiment of the invention, the polyol reactant and the metal hydroxide are first mixed and heated, the epihalohydrin is added to the mixture, heating of the mixture is continued until the reaction is complete, after which an alkali and/or alkaline earth metal halide salt byproduct is removed from the mixture by addition of a lower alkanol to the mixture to precipitate salt, followed by filtration or centrifugation of the mixture, optionally adding additional polyol reactant to a portion of the mixture, further heating the mixture to initiate thermal condensation, removing water formed during the thermal condensation, optionally adding a final quantity of additional polyol reactant when the thermal condensation is within a preselected degree of completion, and continuing the thermal condensation to completion without undergoing degeneration.

This purpose is also achieved by reacting an epoxy alcohol in the presence of an alkali and/or alkaline earth metal hydroxide catalyst, wherein the epoxy alcohol is added to the metal hydroxide catalyst while the mixture is heated, heating of the mixture is continued until the reaction is complete, optionally adding additional polyol reactant to the mixture, further heating the mixture to initiate thermal condensation, removing water formed during the thermal condensation, optionally adding a final quantity of additional polyol reactant when the thermal condensation is within a preselected degree of completion, and continuing the thermal condensation to completion without undergoing degeneration. In another embodiment, the metal hydroxide is first mixed with a solvent and heated, the epoxy alcohol is added to the mixture, heating of the mixture is continued until reaction is complete, optionally adding additional polyol reactant to the mixture, further heating the mixture to initiate thermal condensation, removing water formed during the thermal condensation, optionally adding a final quantity of polyol reactant when the thermal condensation is within a preselected degree of completion, and continuing the thermal condensation to completion without undergoing degeneration. In yet another embodiment of the invention, this purpose is achieved by reacting an epoxy alcohol, and a reactant selected from the group consisting of (a) a polyol having at least two hydroxyl groups, (b) precursors of the polyol, (c) cyclic derivatives of the polyol, and (d) mixtures thereof, in the presence of an alkali and/or alkaline earth metal hydroxide catalyst, wherein the said polyol reactant and the metal hydroxide catalyst are first mixed and heated, the epoxy alcohol is added to the mixture, heating of the mixture is continued until the reaction is complete, optionally adding additional polyol reactant to the mixture, further heating the mixture to initiate thermal condensation, removing water formed during the thermal condensation, optionally adding a final quantity of additional polyol reactant when the thermal condensation is within a preselected degree of completion, and continuing the thermal condensation to completion without undergoing degeneration. In another embodiment, the polyol reactant and the metal hydroxide are first mixed with a solvent and heated, the epoxy alcohol is added to the mixture, heating of the mixture is continued until reaction is complete, optionally adding polyol reactant to the mixture, further heating the mixture to initiate thermal condensation, removing water formed during the thermal condensation, optionally adding a final quantity of additional polyol reactant when the thermal condensation is within a preselected degree of completion, and continuing the thermal condensation to completion without undergoing degeneration. In an additional embodiment of the invention, the polyol reactant and the metal hydroxide are first mixed and heated and water is removed from the mixture, the epoxy alcohol is added to the mixture, heating of the mixture is continued until the reaction is complete, optionally adding additional polyol reactant to the mixture, further heating the mixture to initiate thermal condensation, removing water formed during the thermal condensation, optionally adding a final quantity of additional polyol reactant when the thermal condensation is within a preselected degree of completion, and continuing the thermal condensation to completion without undergoing degeneration.

DESCRIPTION OF PREFERRED EMBODIMENTS

Polyethercyclicpolyols

Polyethercyclicpolyols are those having at least 6 carbon atoms, at least 2 hydroxyl groups, and at least 2 ether linkages, but no more than 1800 carbon atoms, 450 hydroxyl groups, and 600 ether linkages. More preferably, polyethercyclicpolyols are those having at least 15 carbon atoms, 5 ether linkages, and at least 5 hydroxyl groups. Most preferably, polyethercyclicpolyols are those having at least 18 carbon atoms, at least 6 hydroxyl groups, and at least 6 ether linkages, but preferably no more than 1200 carbon atoms, 300 hydroxyl groups, and 400 ether linkages. Weight average molecular weights, $M_w$ (vide infra), preferably range from 50,000 to 200,000. Hereinafter "poly" is used to mean two or more, "mono" is used to mean one, "cyclic" is used to mean one or more ring structures, "ether" is used to mean one or more ether linkages, and polyethercyclicpolyol may also be called PECP or polycyclicpolyetherpolyol.

The preparation of polyethercyclicpolyols via the thermal condensation of polyhydric alcohols has been described in patent applications Ser. Nos. 672,200; 672,199; 672,201; 672,198; 672,203 and 672,202 filed Mar. 19, 1991. In these patent applications, it is disclosed that polyethercyclicpolyols may be prepared by the polycondensation of polyhydric alcohol compounds (vide infra), such as glycerol, telomers of glycerol, such as di-, tri-, tetra-, penta-, and hexaglycerols, mixtures of glycerol and its telomers, precursors of trihydric alcohols, such as glycidol, and derivatives of polyhydric alcohols, such as the bis(hydroxymethyl)-p-dioxanes (vide infra), in chemical processes which are accompanied by significant expulsion of water molecules from the polymerizing compounds. The number of ether linkages equals the number of water molecules expelled. For example, Structure (I) is the lowest molecular weight structure containing two glycerol units.

It is formed by condensing 2 glycerol units, expelling two molecules of water. Alternatively, Structure (I) may be formed by the self-condensation of diglycerol, expelling one molecule of water. Structure (I) may be called 2,6-bis(hydroxymethyl)-p-dioxane, or the cyclic dimer of glycerol. Similarly, condensing two Structure (I) units yields Structure (II), containing two terminal hydroxyl groups and five ether linkages.

(II)

Structure (II) may also be formed by condensation of four glycerol units with the expulsion of five water molecules. This structure is a dicyclic- poly (or penta) etherdiol, and may be called di-bis(hydroxymethyl)-p-dioxane. Polyethercyclicpolyols may also be formed by further condensation or polycondensation of Structure (II) with itself, or with itself and with polyhydric, at least trihydric monomers, such as glycerol monomers. Dimerization of Structure (II) with expulsion of one molecule of water yields Structure (III).

(III)

Copolycondensation of four Structure (I) units with itself and with one glycerol molecule can yield Structure (IV) and its isomeric equivalents.

(IV)

Structure (IV) contains twelve ether linkages, three hydroxyl groups, and four six-membered cyclic diethers, and is formed by the polycondensation of nine glycerol molecules with the expulsion of twelve water molecules. The cyclic diether units and the polycondensed glycerol units, or other polyhydric units, occur randomly in the structure. Disregarding the order of occurrence, a general chemical composition formula representative of all these structures is given by Structure (V).

(V)

where $x>1$ and $y>0$.

In the present case it is disclosed that polyethercyclicpolyols with the same chemical structures may also be prepared via a novel synthetic route consisting of the addition of epihalohydrins to polyhydric alcohol compounds (vide infra) (such as glycerol, telomers of glycerol, such as di-, tri-, tetra-, penta- and hexaglycerol, and derivatives of polyols, such as the bis(hydroxymethyl)-p-dioxanes) in the presence of stoichiometric amounts of alkali and/or alkaline earth metal hydroxide in a one-step process.

It is theorized, although the invention is not limited to this theory, that this process is composed of a three chemical step reaction cycle: addition, followed by dehydrohalogenation, followed by addition, in which a molecule containing an epoxy functionality reacts with a molecule containing a hydroxyl functionality to yield a molecule containing a hydroxyl group attached to a carbon in the alpha position to another carbon which is bound to a halide atom. Such a molecule may be called a halohydrin. The halohydrin may then react with a metal hydroxide in a dehydrochlorination reaction to yield a molecule with an epoxy functionality, along with metal halide salt and water as byproducts. The new product molecule with the epoxy functionality may then undergo a further addition reaction to another molecule containing a hydroxyl group. Repetitions of this cycle in which di- or polyfunctional product molecules containing one or more hydroxyl groups react with additional epihalohydrin reactant may form molecules of high molecular weight. As a non-limiting, illustrative example of this reaction sequence, epichlorohydrin may react with glycerol to produce a chlorohydrin compound, Structure (VI), containing an ether linkage and a terminal hydroxyl group in Equation (1).

(1)

(VI)

The chlorohydrin (VI) may react with sodium hydroxide to produce a glycidyl ether, Structure (VII), as shown in Equation (2). Sodium chloride and water are byproducts of the reaction.

(2)

(VII)

The glycidyl ether (VII) may then react with another molecule of glycerol to produce a larger molecule with two ether linkages and two terminal hydroxyl groups, Structure (VIII), in Equation (3).

(3)

(VII)

(VIII)

In general, any polyhydric alcohol (vide infra) may substitute for glycerol in Equations (1)–(3). Thus, since glycerol and other polyhydric alcohols are multi-functional, polymeric ethers may be formed by repeating the three step chemical reaction sequence shown in Equations (1)–(3), since the reaction product contains two terminal hydroxyl functionalities and thus may substitute for the polyhydric alcohol monomer in Equation (1).

Theoretically, the molar ratio of polyhydric alcohol monomer to epihalohydrin for a linear chain of infinite length approaches one. However, other reactions may occur simultaneously in the mixture. For example, crosslinking or branching in the product polyethercyclicpolyol may occur by reacting the non-terminal hydroxyl groups on the polyhydric alcohol. It is theorized, although the invention is not limited to this theory, that the non-terminal (internal or secondary or tertiary) hydroxyls, react less readily with the epoxy group than the terminal (or primary) hydroxyls. Further, it may be possible to control the relative amount of crosslinking by varying the reaction parameters (vide infra).

Still other reactions may also occur in the mixture. In particular, hydrolysis may occur, as shown for Structure (VII) in Equation (4).

(VII)

(IX)

The product, Structure (IX), contains two terminal hydroxyls and no epoxy functionality. In general, increasing amounts of water in the reaction mixture lead to increased occurrence of hydrolysis, and thus a lower molecular weight product is obtained. However, the hydrolysis of epihalohydrin, followed by dehydrohalogenation, is theorized to be an important reaction for the production of the intermediate which is the source of the cyclic ether building unit or monomer of polyethercyclicpolyol, although the invention is not limited to this theory. These reactions are illustrated for the hydrolysis of epichlorohydrin to glycidol in Equations (5) and (6).

Glycidol may dimerize to produce the cyclic ethers which are called bis(hydroxymethyl)-p-dioxanes, shown in Equation (7). Such cyclic ether units are thought to be essential for the good performance of polyethercyclicpolyols as drilling fluid additives.

These cyclic ether units each contain two terminal hydroxyl groups, and thus may enter into addition reactions with epoxy functionalities on other molecules, thus incorporating the cyclic diether rings into the polyethercyclicpolyol product, as shown in Equation (8).

(X)

The product (X) may further undergo dehydrochlorination to yield a molecule with a terminal epoxy functionality. This epoxy functionality may then undergo further addition reactions with hydroxyl groups. The terminal hydroxyl functionality in (X) is also available for addition reactions with epoxy functionalities. Thus, repeating the addition-dehydrochlorination-addition reaction sequence may be expected to yield polyethercyclicpolyols of chemical composition represented by the formula given for Structure (V) (vide supra).

Alternatively, glycidol may be further hydrolyzed to glycerol, shown in Equation (9).

In the present case it is also disclosed that polyethercyclicpolyols with the same chemical structures may also be prepared via a novel synthetic route consisting of the addition of epoxy alcohols to themselves and/or optionally to polyhydric alcohol compounds (vide infra) (such as glycerol, telomers of glycerol, such as di-, tri-, tetra-, penta- and hexaglycerol, and derivatives of polyols, such as the bis(hydroxymethyl)-p-dioxanes) in the presence of catalytic amounts of alkali and/or alkaline earth metal hydroxide in a one-step process.

It is theorized, although the invention is not limited to this theory, that epoxy alcohols with the hydroxyl group bound to a carbon atom adjacent to a carbon atom bonded to the epoxy oxygen atom (e.g. especially glycidol) may dimerize to produce the cyclic ethers which are called bis(hydroxymethyl)-p-dioxanes, as illustrated in Equation (7) for glycidol, the preferred epoxy alcohol (vide supra). Such cyclic ether units are thought to be essential for the good performance of polyethercyclicpolyols as drilling fluid additives.

These cyclic ether units each contain two terminal hydroxyl groups, and thus may enter into addition reactions with epoxy functionalities on other molecules, thus incorporating the cyclic diether rings into the polyethercyclicpolyol product, as illustrated in Equation (8) (vide supra).

The terminal hydroxyl functionality in (X) is also available for addition reactions with epoxy functionalities. For example, the product (X) may further undergo addition with another epoxy alcohol molecule to yield a polyethercyclicpolyol with a higher molecular weight. When no polyol is reacted, this reaction scheme is expected to primarily produce polyethercyclicpolyols with one cyclic structure incorporated per molecule. When cyclic-containing polyols are used, the cyclic structures present in the polyol are incorporated into the product polyethercyclicpolyol. Thus, the dimerization-addition reaction sequence may be expected to produce polyethercyclicpolyols of chemical composition represented by the formula given for Structure (V) (vide supra). When linear (non-cyclic-containing) polyols are used, the amount of polyol used must be limited in order to obtain a polyethercyclicpolyol with sufficient cyclic content.

Since epoxy alcohols may be hydrolyzed by reaction with water, for example, the glycidol hydrolysis to glycerol, shown in Equation (9), the water concentration in these reactions will have an effect on the molecular weight of the product polyethercyclicpolyols.

Further, epoxy alcohols may also self-react to produce linear oligomers. For example, glycidol may self-react to produce polyglycerol, as shown in Equations (10) and (11).

(10)

(11)

Polyhydric Alcohols

Polyhydric alcohols that are at least dihydric are required. The water solubility of the polyethercyclicpolyol product may depend on the polyol used, however. Thus, glycols, triols, tetrols, etc. are suitable reactants. Nonlimiting examples include ethylene glycol, diethylene glycol, triethylene glycol, tetraethylene glycol, polyethylene glycols, propylene glycol, butanediols, pentanediols, hexanediols, glycerol (which is the preferred polyol reactant), telomers of glycerol, such as diglycerols, triglycerols, tetraglycerols, pentaglycerols, and hexaglycerols, mixtures of glycerol and telomers of glycerol such as diglycerols and triglycerols, 1,5,6,9-decanetetriol; 1,2,4,5-cyclohexanetetramethanol; 1,2,4,7-heptanetetriol; 1,2,3,5-heptanetetriol; 4,4-dimethyl-1,2,3-pentanetriol; 1,3,4-cycloheptanetetriol; 1,2,3-pentanetriol; 1,2,4-pentanetriol; 2,3,4-pentanetriol; 1,1-cyclopentanediol; 1,2,3-cyclopentanetriol; 1,2,3-hexanetriol; 1,2,4-hexanetriol; 1,2,3,4-hexanetetriol; 1,2,4-cyclohexanetriol; 1,2,5-cyclohexanetriol; 1,2,3,4-cyclohexanetetriol; 1,2,3,5-cyclohexanetetriol; sorbitol; mannitol, 2,5- and 2,6-bis(hydroxymethyl)-p-dioxanes, copolymers of ethylene glycol and propylene glycols with the preceding alcohols, and mixtures of the preceding alcohols. An important class of polyhydric alcohols with straight carbon chains and four or more hydroxyl groups, called sugar alcohols, can also be used in preparing additive formulations containing cyclic polyethers. Sorbitol and mannitol are two such well-known polyhydric alcohols.

Precursors of trihydric polyols are also suitable reactants. For example, glycidol, an epoxy alcohol (vide supra) which upon reaction with water hydrolyzes to give glycerol, is an excellent reactant. Similarly, 3,4-epoxy-1-butanol is also an excellent reactant. The preferred structure of polyol precursors is given by Structure (XI)

(XI)

where R=H, OH, 1–12C alkyl, cycloalkyl, aryl, alkaryl, or aralkyl and x>1 and y>0, with the condition that when y=0, then R=H.

Derivatives of polyols are also useful feeds. For example, derivatives of glycerol, including linear and cyclic dimers, such as cis- or trans-2,5-bis(hydroxymethyl)-p-dioxane (XII), cis- or trans-2,6-bis(hydroxymethyl)-p-dioxane (XIII), and the glycerine acetal of hydracrylaldehyde (XIV) can react with epihalohydrins to produce polyethercyclicpolyols.

(XII)

(XIII)

(XIV)

Known commercial mixtures of bis(hydroxymethyl)-p-dioxanes and polyols, especially glycerol, can react with epihalohydrins to produce polyethercyclicpolyols. Polyols, for example polyglycerols, are suitable reactants. Footstill bottoms (heavy ends from the manufacture of glycerol) are mixtures of glycerol, bis(hydroxymethyl)-p-dioxanes, linear polyglycerols, and small amounts of low molecular weight polyethercyclic-polyols, and are useful as a polyol reactant.

Byproducts or effluent streams from other existing processes for which the principal products are resins, soaps, and the like, can be excellent feedstocks. Exemplary are process streams of glycerol/glycidol mixtures which may contain other components, for example, mixtures of glycerol, glycidol, epichlorohydrin, dimethyl ketone, isopropyl alcohol, and/or sodium chloride made in the manufacture of resins. Such streams may first be processed to remove the nonglycerol-related material, for example, sodium chloride and/or water. Effluent streams from processes such as resin manufacture fit this category of feedstock. Such streams may contain predominantly water and salt (10 to 15 percent by weight), with small amounts of glycerol, glycidol, bis(hydroxymethyl)-p-dioxanes, and polyethercyclicpolyols of low molecular weight (and therefore initially ineffective for use in drilling fluids). For example, in an existing plant, the components of an effluent stream are 12 to 15 percent by weight sodium chloride, 0.3 to 2 percent by weight glycerol, 0.3 to 1.2 percent by weight glycidol, and less than 0.5 percent by weight polyglycerols, bis(hydroxymethyl)-p-dioxanes, and low molecular weight polyethercyclicpolyols, with the balance being water.

Epihalohydrins

Epihalohydrins are compounds which contain an epoxy group and a halogen in the vicinal position to the epoxy group. This is represented by Structure (XV).

where X = Cl, Br, I, F

In general, any epihalohydrin, such as epichlorohydrin, epibromohydrin, epiiodohydrin, and epifluorohydrin, may be used in the preparation of polyethercyclicpolyols, and may substitute for epichlorohydrin in Equations (1)–(3). The preferred epihalohydrin is epichlorohydrin.

Epoxy Alcohols

Epoxy alcohols are compounds which contain at least one epoxide and one or more hydroxyl groups. The preferred structure of epoxy alcohols is represented by Structure (XVI).

where $R^1$, $R^2$, $R^3$ and $R^4$ independently = H, alkyl, aryl and $x > 0$

In general, any epoxy alcohol, such as 1,2-epoxybutan-3-ol and 1,2-epoxybutan-4-ol, may be used in the preparation of polyethercyclicpolyols, and may substitute for glycidol in Equations (1)–(3). The preferred epoxy alcohol is glycidol. The amount of epoxy alcohol used is preferably 75 to 99.9 (more preferably 85–99.5) weight percent of the total reaction mixture.

The addition of epoxy alcohols and polyhydric alcohols is similar in some aspects to the addition of epihalohydrins and polyhydric alcohols in the presence of alkali metal hydroxide as described in concurrently filed application Serial No. 960,160, filed Oct. 13, 1992, now abandoned. An advantage of the process described herein is that there are no by-products of the reaction with epoxy alcohol, such as alkali metal halide and/or water, and therefore the sometimes elaborate procedures required for the removal of by-products are unnecessary.

Alkali Metal or Alkaline Earth Metal Hydroxides

Alkali metal hydroxides have the general formula MOH, where M = Na, K, Li, Rb and Cs. Alkaline earth metal hydroxides have the general formula $M'(OH)_2$, where M' = Ca, Mg, Sr, Be, and Ba. In general, any alkali metal and/or alkaline earth metal hydroxide, such as sodium hydroxide, potassium hydroxide, lithium hydroxide, rubidium hydroxide, cesium hydroxide, calcium hydroxide, magnesium hydroxide, barium hydroxide, strontium hydroxide, or beryllium hydroxide, may be used in the preparation of polyethercyclicpolyols, and may substitute for sodium hydroxide in Equations (1)–(3). Preferably, sodium hydroxide, potassium hydroxide, lithium hydroxide, calcium hydroxide, or magnesium hydroxide is the metal hydroxide. Most preferably, sodium hydroxide or potassium hydroxide is the metal hydroxide.

Epoxy Resins

In accordance with the present invention it has been found that the addition of minor amounts of epoxy resins are beneficial. Epoxy resins are characterized by the presence of a three-membered cyclic ether group commonly referred to as an epoxy group, 1,2-epoxide, or oxirane. Preferred epoxy resins are diglycidyl ethers, triglycidyl ethers, and tetraglycidyl ethers which, when added either to a polyol-epihalohydrin-metal hydroxide reaction medium or an epoxy alcohol-polyol reaction medium, result in the formation of higher molecular weight polyethercyclicpolyols with substantially improved properties in connection with drilling fluid performance.

A particularly useful epoxy is a difunctional glycidyl ether such as "EPON 828" (a trademark of Shell Oil Company) which it is theorized, although the invention is not limited to this theory, significantly increases the average molecular weight of the polyethercyclicpolyols preparation. Thus, addition of 3 weight percent of "EPON 828" could result in doubling the molecular weight of between 10 and 20 percent of the preparation. By thus increasing the molecular weight of a significant portion of the preparation, the co-addition of "EPON 828" is thought to result in significantly boosting the $M_w$ value of the sample, with attendant significant improvements in the performance of the resulting polyethercyclicpolyols/polyethercyclicpolyols-diglycidyl ether mixture. In order to obtain polyethercyclicpolyols with maximum coverage potential, it is suitable to use tri- and tetraglycidyl ethers which will direct addition along more than one direction in a planar configuration. It is theorized, although the invention is not limited to this theory, that the use of such epoxies facilitates the coverage of openings in the clay surface of an oil well through which water can enter the clay. Thus, it is believed that molecules which are substantially planar in structure are most useful with the invention when it is employed as part of a drilling fluid additive. Additionally, the attachment of several polyethercyclicpolyols onto the same central molecule of polyglycidyl ether allows multiple coordination of cationic species to occur through the electron-donating oxygen atoms in the ether linkages, which results in formation of large molecular aggregates that can inhibit the migration of water molecules from the aqueous phase of the water-based drilling mud onto the hydrophilic clay solids of the formation. Conventional drilling muds containing polyethercyclicpolyols act essentially in a manner similar to that of oil-based muds. This theory, of course, is not limiting of the application of this invention.

The following epoxies are considered useful in the present invention (but the invention is not limited to these epoxies):

"EPON 828" (trade name for epoxy manufactured by Shell Oil Company)

"TACTIX 742" (trade name for epoxy manufactured by Dow Chemical Company)

"EPON 1031" (trade name for epoxy manufactured by Shell Oil Company)

"HELOXY 67" (trade name for epoxy manufactured by Rhone-Poulenc)

"HELOXY 69" (trade name for epoxy manufactured by Rhone-Poulenc)

"HELOXY 107" (trade name for epoxy manufactured by Rhone-Poulenc)

"HELOXY 5044" (trade name for epoxy manufactured by Rhone-Poulenc)

It is preferred to add the material to the reaction mixture in two or three aliquots, after the epihalohydrin or epoxy alcohol addition is at least 50 percent complete. Alternately, the epoxy resin may also be combined with the epihalohydrin or epoxy alcohol prior to addition to the polyol-metal hydroxide mixture or polyol, respectively.

Process Conditions

The preparation of polyethercyclicpolyols via thermal condensation of of polyhydric alcohols has been described in patent applications Ser. Nos. 72,203; 672,202; 672,200; 672,199; 672,201 and 672,198 filed Mar. 19, 1991. In the thermal condensation reaction, a predetermined quantity of moles of water per mole of reactant are removed. In contrast, in the present invention, for polyethercyclicpolyols produced from epihalohydrins, polyhydric alcohols and metal hydroxides, while water is a byproduct of the dehydrochlorination reaction (vide supra), no specific quantity of water need be removed from the reaction mixture. Instead, a specified molar ratio of epihalohydrin to polyol (vide infra) is preferred for the preparation of polyethercyclicpolyols. Alternatively, for polyethercyclicpolyols produced from epoxy alcohols and optionally polyhydric alcohols, water is not produced in the reaction sequence (vide supra), and thus water need not be removed from the reaction mixture. Instead, a specified molar ratio of epoxy alcohol to polyol (vide infra) is preferred for the preparation of polyethercyclicpolyols. The thermal condensation reaction must be conducted at subatmospheric pressures to assist in removing the water of condensation. In the present invention, the reaction is typically carried out at atmospheric conditions, although reduced pressures may be used if desired. The onset of the thermal condensation reactions occur above 210° C. In contrast, the addition reactions described in the present invention occur at much lower temperatures, specifically 50° C.–200° C. In the thermal condensation, additional reactant is added as the degree of condensation increases, and the reaction is initially endothermic, becoming exothermic only as the reaction nears completion. In the present invention, the epihalohydrin reactant (or alternatively the metal hydroxide reactant) or the epoxy alcohol reactant is added slowly to control the reaction temperature since the addition reaction is exothermic. Finally, in the thermal condensation, only polyols are used which have at least three hydroxyl groups of which are least two of the hydroxyl groups are vicinal. In contrast, in this present invention, polyols which have at least two hydroxyl groups may be employed.

Seven variables appear to affect the molecular weight and cyclic content of the product polyethercyclicpolyols: 1) the concentration of epihalohydrin or epoxy alcohol in the reaction mixture at a given time (or the addition rate), 2) the molar epihalohydrin or epoxy alcohol to polyol ratio, 3) the concentration of alkali and/or alkaline earth metal hydroxide in the reaction mixture, 4) the concentration of water in the reactants, solvent and/or reaction mixture at a given time, 5) solvent type and amount, 6) reaction temperature, and 7) reaction time.

Epihalohydrins and epoxy alcohols are hazardous chemicals which must be handled with great care; special precautions and procedures were used in these preparations. The epihalohydrin or epoxy alcohol is usually added to reaction mixtures slowly (either in a slow, continuous flow or portionwise) in order to control the reaction temperature, since the reaction of epihalohydrin or epoxy alcohol with polyols is exothermic (as are most reactions of epoxy groups). Besides controlling the temperature, the slow addition rate has the added benefit of regulating undesired side reactions which may increase in importance when the epihalohydrin or epoxy alcohol concentration in the mixture is high. Alternatively, the metal hydroxide reagent may be added slowly to a mixture of polyol and epihalohydrin with similar results to that described above.

The Epihalohydrin/Polyol/Metal Hydroxide Process

The epihalohydrin/polyol molar ratio employed varies with the nature of the polyol used. Normally an excess of epihalohydrin above the stoichiometric molar ratio of one predicted for a linear polymer of infinite length is preferred. This is because of the competing desired cyclization reaction and both the desired and undesired hydrolysis reactions described earlier. However, if a polyol reactant is employed which already has a moderate molecular weight and/or already contains some cyclic ether structures, for example, a low molecular weight polyethercyclicpolyol that one is trying to upgrade, or a byproduct stream which is composed of approximately 85 percent glycerol and 15 percent bis(hydroxymethyl)-p-dioxanes, a molar epihalohydrin/polyol ratio of less than one may be desired. Thus, an epihalohydrin/polyol molar ratio of 0.3–3.0 is preferred, with 0.70–2.0 being most preferred.

The reaction consumes metal hydroxide stoichiometrically with epihalohydrin; however, an excess of metal hydroxide is used in practice. A metal hydroxide/epihalohydrin molar ratio of 1.0–4.0 is preferred, with 1.05–1.55 being most preferred. Solid metal hydroxide is preferably used to control the concentration of water in the reaction mixture, although concentrated (e.g. 50% weight) aqueous solutions of metal hydroxide may also be used as the metal hydroxide source instead of the solid.

Solid metal hydroxide is generally added to the polyol at the beginning of the reaction. This addition is exothermic; reaction occurs between the metal hydroxide and the polyol to produce metal alkoxide and water. When the mixture is heated, the reaction is accelerated, especially if water is removed from the mixture. A thick, pasty white solid is formed. At least part of the polyol is likely converted to its alkali and/or alkaline earth metal salt.

The amount of water present at the beginning of the reaction has a large effect in a practical sense. With some polyols the reaction mixture becomes a concrete-like solid mass just after epihalohydrin addition is started, unless some water is added to the mixture. The solidification of the polyol/metal hydroxide mixture can also occur without any epihalohydrin addition by heating the mixture above 135° C. The fluidity of the mixture can be restored by adding a small amount of water. The water concentration in the mixture at any given time is a critical variable because of the various hydration reactions that can occur, leading to low molecular weight products. The effect of this variable may depend on other reaction variables, for example, the type and amount of solvent used or the epihalohydrin/polyol ratio.

In principle, water added to the reactions can be minimized (in order to maximize the average molecular weight of the polyethercyclicpolyol) without sacrificing fluidity by using a solvent. The use of a solvent is, however, optional; polyethercyclicpolyols may be prepared without the use of a solvent. Acetone is the preferred solvent. Other solvents, including ketones, ethers and hydrocarbons, such as methyl ethyl ketone, toluene and diglyme may also be used. Alcohols, especially mono-alcohols, will react with the epoxy alcohol in addition reactions, and thus alcohols are not suitable solvents. Similarly, compounds containing other functional groups, such as amines, which are reactive with epoxy groups, are not useful as solvents for the reaction. The weight ratio of solvent/polyol used is preferably 0.05–20, and is most preferably 0.5–10. Acetone is not a good solvent for the metal hydroxide/polyol mixture in the absence of water; the reaction mixture is inhomogeneous. In this inhomogeneous mixture, reaction to form polyethercyclicpolyols will still occur. The mixture with acetone can be made homogeneous, however, by the addition of small amounts of water.

The use of a solvent such as acetone may also increase the cyclic content of polyethercyclicpolyols. In these reactions, the polyol/metal hydroxide is only slightly soluble in the acetone, and the resulting mixture is a two-phase mixture. It is theorized, although the invention is not limited to this theory, that inhomogeneity of the mixture promotes the formation of cyclic bis(hydroxymethyl)-p-dioxane units, since the epihalohydrin is soluble in the acetone phase, which appears to contain little of the metal hydroxide/polyol mixture. This may enhance the occurrence of cyclization reactions.

The reaction temperature varies with the solvent that is chosen. If acetone is used as the solvent, the mixture will initially reflux at or near 58° C., with the temperature of reflux increasing gradually as the reaction occurs. The temperature range is preferably 50° C.–200° C., most preferably 58° C.–150° C. Condensate from the vapor may be returned to the reaction mixture, or a portion of it may be withdrawn. The condensate is typically a mixture of water (formed in the dehydrochlorination reaction), epihalohydrin and solvent, if solvent is used. The reaction is generally conducted under atmospheric conditions, although it may be conducted under reduced pressure if desired.

The reaction time has been found to be a significant reaction variable; sufficient time must be allowed for all the epihalohydrin to react. Preferably, the desired reaction temperature is maintained for 10–300 minutes after epihalohydrin addition is complete, and most preferably for 20–180 minutes. Incomplete reaction may be evidenced directly by analysis of the reaction mixture for unreacted epihalohydrin, or indirectly by the requirement of an excess of acid above that theoretically required to neutralize the metal hydroxide remaining after reaction.

Part of the metal halide salt byproduct may also be removed by precipitation through the addition of a lower alkanol, such as n-propanol, methanol, n-butanol or n-pentanol. As the average molecular weight of the polyethercyclicpolyol samples increases, however, this salt extraction becomes less feasible; much of the product may precipitate with the solid salt.

A typical polyethercyclicpolyol preparation is carried out as follows: a 500 ml 4-neck resin kettle is fitted with a thermocouple, a nitrogen inlet, a metering addition funnel, an air-driven stirrer and a condenser (optionally fitted with a distillation head for solvent recovery). Preparations are optionally conducted under a low nitrogen flow at atmospheric pressure. The reactions may also optionally be run under reduced pressure to facilitate removal of water from the system.

Polyalcohol (for example, glycerol), solvent (if used, preferably acetone) and metal hydroxide (preferably sodium or potassium hydroxide) are added to the flask. The mixture is stirred and heated. The reaction temperature is preferably 50° C.–200° C., and is most preferably 55° C.–160° C. The reaction temperature depends on the solvent used. When acetone is the solvent, the reaction temperature is held lower by the acetone refluxing. When no solvent is used, the mixture temperature can easily rise above 140° C. The specific effect of reaction temperature on the product molecular weight and composition is unknown.

After the mixture reaches the desired reaction temperature, epihalohydrin (preferably epichlorohydrin) is then added dropwise from the addition funnel. Temperature control is achieved via evaporative cooling. Condensate water may be withdrawn or recycled to the flask. It may be necessary to add water as required to maintain a fluid mixture especially if water is removed from the reaction as it is formed.

The mixture is stirred at least 90 minutes after the epihalohydrin addition is complete. Concentrated mineral acid, preferably hydrochloric, phosphoric or sulfuric acid, is added to neutralize the excess metal hydroxide and/or adjust the mixture pH to a desired value. The amount of acid used may be calculated from the excess of metal hydroxide employed. Low boiling solvent, if used, is then distilled from the mixture. Some of the water added to or formed in the reaction may also be removed by distilling under reduced pressure at this point.

If removal of part of the salt byproduct is desired, a lower alkanol, preferably methanol, n-propanol, n-butanol or n-pentanol, is added to the warm mixture with stirring. The mixture is removed from the flask and centrifuged at 3500 rpm for 45 minutes. (Alternatively, the precipitated salt may be removed by filtration.) The centrifuged mixture often comprises two or three layers. When there are three layers, the top layer contains mostly n-alkanol and light ends, the middle layer is mostly polyethercyclicpolyol and the bottom layer is mostly salt. The middle layer is then evaporated at >120° C. and 20 mm Hg until no more water or solvent are removed.

The product from this addition process is then thermally condensed (vide infra) to form a polyethercyclicpolyol of higher molecular weight and greater degree of cyclicity.

The Epoxy Alcohol/Polyol Process

In the epoxy alcohol addition reaction, the use of a polyol reactant is optional. When polyol is used, the epoxy alcohol/polyol molar ratio employed varies with the nature of the polyol used. Normally a large molar excess of epoxy alcohol over polyol is preferred. In general, a low epoxy alcohol/polyol molar ratio will lead to a low molecular weight product. This is because there is no mechanism (such as dehydrochlorination in the reaction using epihalohydrins) to regenerate the reactive epoxy functionality. However, if a polyol reactant is employed which already has a moderate molecular weight and/or already contains some cyclic ether structures, for example, a low molecular weight polyethercyclicpolyol that one is trying to upgrade, a lower molar epoxy alcohol/polyol ratio may be desired. Thus, an epoxy alcohol/polyol molar ratio of 5–1500 is preferred, with 10–500 being most preferred.

Unlike the addition of epihalohydrins and polyols in the presence of metal hydroxide to produce polyethercyclicpolyols, which consumes metal hydroxide stoichiometrically with epihalohydrin, the addition of epoxy alcohols and polyols uses metal hydroxide catalytically. A metal hydroxide/epoxy alcohol molar ratio of 0.005–0.5 is preferred, with 0.01–0.2 being most preferred. Solid metal hydroxide is preferably used to control the concentration of water in the reaction mixture, although concentrated (e.g. 50% weight) aqueous solutions of metal hydroxide may also be used at the metal hydroxide source instead of the solid.

Solid metal hydroxide catalyst is generally added to the polyol (if used) at the beginning of the reaction. This addition is exothermic; reaction occurs between the metal hydroxide and the polyol to produce metal alkoxide and water. When the mixture is heated, the reaction is accelerated, especially if water is removed from the mixture. A thick, pasty white solid is formed. At least part of the polyol is likely converted to its alkali and/or alkaline earth metal salt.

If polyol is not used, the solid metal hydroxide may be slurried in an appropriate solvent (vide infra) or in the epoxy alcohol itself.

Acidic catalysts, such as boron trifluoride and other Lewis acids, are not effective catalysts for the production of polyethercyclicpolyols. It is theorized, although the invention is not limited to this theory, that acidic catalysts do not effectively catalyze the dimerization or cyclization reaction of epoxy alcohols.

The amount of water present at the beginning of the reaction has a large effect in a practical sense. With some polyols the reaction mixture may become very hard or viscous after the metal hydroxide-polyol mixture is heated, especially above 100° C., unless some water is added to the mixture. The fluidity of the mixture can be restored by adding a small amount of water. The water concentration in the mixture at any given time is a critical variable because of the various hydration reactions that can occur, leading to low molecular weight products. The effect of this variable may depend on other reaction variables, for example, the type and amount of solvent used or the epoxy alcohol/polyol ratio.

In principle, water added to the reactions can be minimized (in order to maximize the average molecular weight of the polyethercyclicpolyol) without sacrificing fluidity by using a solvent. The use of a solvent is, however, optional; polyethercyclicpolyols may be prepared without the use of a solvent. Acetone is the preferred solvent. Other solvents, including ketones, ethers and hydrocarbons, such as methyl ethyl ketone, toluene and diglyme may also be used. Alcohols, especially mono-alcohols, will react with the epoxy alcohol in addition reactions, and thus alcohols are not suitable solvents. Similarly, compounds containing other functional groups, such as amines, which are reactive with epoxy groups, are not useful as solvents for the reaction. The weight ratio of solvent/epoxy alcohol used is preferably 0.05–20, and is most preferably 0.5–10. Acetone is not a good solvent for the metal hydroxide/polyol mixture in the absence of water; the reaction mixture is inhomogeneous. In this inhomogeneous mixture, reaction to form polyethercyclicpolyols will still occur. The mixture with acetone can be made homogeneous, however, by the addition of small amounts of water.

The use of a solvent such as acetone may also increase the cyclic content of polyethercyclicpolyols. In these reactions, the polyol/metal hydroxide is only slightly soluble in the acetone, and the resulting mixture is a two-phase mixture. It is theorized, although the invention is not limited to this theory, that inhomogeneity of the mixture promotes the formation of cyclic bis(hydroxymethyl)-p-dioxane units, since the epoxy alcohol is soluble in the acetone phase, which appears to contain little of the metal hydroxide/polyol mixture. This may enhance the occurrence of dimerization reactions.

The reaction temperature varies with the solvent that is chosen. If acetone is used as the solvent, the mixture will initially reflux at or near 58° C., with the temperature of reflux increasing gradually as the reaction occurs. The temperature range is preferably 50° C.–200° C., most preferably 58° C.–150° C. Condensate from the vapor may be returned to the reaction mixture, or a portion of it may be withdrawn. The condensate is typically a mixture of water (from wet reactants), epoxy alcohol and solvent, if solvent is used. The reaction is generally conducted under atmospheric conditions, although it may be conducted under reduced pressure if desired.

The reaction time has been found to be a significant reaction variable; sufficient time must be allowed for all the epoxy alcohol to react. Preferably, the desired reaction temperature is maintained for 10–300 minutes after epoxy alcohol addition is complete, and most preferably for 20–180 minutes. Incomplete reaction may be evidenced directly by analysis of the reaction mixture for unreacted epoxy alcohol.

A typical polyethercyclicpolyol preparation is carried out as follows: a 500 ml 4-neck resin kettle is fitted with a thermocouple, a nitrogen inlet, a metering addition funnel, an air-driven stirrer and a condenser (optionally fitted with a distillation head for solvent recovery). Preparations are optionally conducted under a low nitrogen flow at atmospheric pressure. The reactions may also optionally be run under reduced pressure to facilitate removal of residual water from the system.

Polyalcohol (if used, for example, glycerol), solvent (if used, preferably acetone) and metal hydroxide (preferably sodium or potassium hydroxide) are added to the flask. The mixture is stirred and heated. The reaction temperature is preferably 50° C.–200° C., and is most preferably 55° C.–160° C. The reaction temperature depends on the solvent used. When acetone is the solvent, the reaction temperature is held lower by the acetone refluxing. When no solvent is used, the mixture temperature can easily rise above 140° C. The specific effect of reaction temperature on the product molecular weight and composition is unknown.

After the mixture reaches the desired reaction temperature, epoxy alcohol (preferably glycidol) is then added dropwise from the addition funnel. Temperature control is achieved via evaporative cooling. It may be necessary to add water as required to maintain a fluid mixture.

The mixture is stirred at least 90 minutes after the epoxy alcohol addition is complete. Low boiling solvent, if used, is then distilled from the mixture. Some of the water added to the reaction may also be removed by distilling under reduced pressure at this point.

The product from this addition process is then thermally condensed (vide infra) to form a polyethercyclicpolyol of higher molecular weight and greater degree of cyclicity.

Thermal Condensation

In a typical preparation in accordance with the invention, a polyethercyclicpolyol consisting of the product of the addition of epihalohydrin (preferably epichlorohydrin) and polyol (preferably glycerol) in the presence of a metal hydroxide (preferably sodium or potassium hydroxide) and/or the product of the addition of epoxy alcohol (preferably glycidol) and polyol (preferably glycerol), preferably containing small amounts of catalyst such as sodium hydroxide, preferably along with small amounts of sodium acetate, are reacted in distillation apparatus under conditions which allow water to be removed overhead, but not substantial amounts of glycerol or its dimers and trimers. The catalyst, alkali metal hydroxide, preferably sodium hydroxide, is in a preferred concentration of 0.5 to 1.5 percent by weight of the reaction mixture and alkali metal acetate, preferably sodium acetate, in like or smaller amounts. Other suitable catalysts include potassium, lithium or calcium hydroxide or other condensation catalysts, such as sodium tungstate or tin (IV) chloride.

The starting pH for the condensation reaction ranges from 5 to 13.5 and preferably ranges from 8 to 10. The pH gradually declines during the process to 5 to 9.5 and preferably to 6.5 to 9. The materials removed overhead in the distillation are acidic to neutral and have pH ranging from 3 to 7.

The reaction mixture is heated under a pressure of at least 100 mm Hg, and preferably between 150 and 300 mm Hg. (For glycerol, more preferably a pressure of 160 to 230 mm Hg is used.) Under these conditions, any free water will be distilled off. Moreover, water produced by the condensation reactions will be distilled off continuously, allowing the equilibrium-limited condensation reaction to proceed further and to completion. Water removal may be facilitated by bubbling an inert gas, such as nitrogen, through the mixture. Such bubbling will also ensure through mixing. The mixture may also be continuously stirred to ensure thermal equilibrium throughout. The dry polyethercyclicpolyol will then begin to rise in temperature to about 210° to 230° C. at 150 to 300 mm Hg, at which temperature the mixture refluxes, indicating the onset of reactions which produce water by condensation of the molecules. By maintaining a pressure of at least 160 mm Hg, any lights which may volatilize along with the water are condensed in an overhead condenser, which is preferably cooled by a coolant such as water/glycol mixtures. These lights, which may be for example glycerol and its linear and cyclic dimers, which form in the course of the volatilization process, are thus condensed and refluxed to the reacting mixture. Gradually the procedure results in an increase in the boiling point of the mixture, brought about by the continuous removal of water of condensation and by the increase of the molecular weight of the mixture.

Epoxy resin is optionally added to the reaction mixture in two or three aliquots. The weight of epoxy resin added is preferably 0.05–25 (and more preferably 0.25–10) weight percent of the total weight of the reactants, excluding the solvent, if used.

As the degree of the polymerization increases, and the amount of water removed from the polyethercyclicpolyol feed increases, the pressure over the mixture is gradually decreased externally, either in a continuous, preferably gradual, mode, or at selected reaction temperatures. For example, it is possible to reduce the pressure to 120 mm Hg. Or alternatively, it is possible to control the pressure to diminish gradually by known mechanical means. A stepwise pressure reduction may be used, for example: 180 mm Hg to 120 mm Hg to 80 mm Hg to 60 mm Hg.

The degree of dehydration during the procedure is monitored in terms of moles of water removed per mole of glycerol left in the product. As the ratio of moles of water removed per mole of glycerol in the product increases, the degree of polymerization of glycerol increases, and the number average molecular weight of the mixture increases. Particularly important is the discovery of the strong relationship between the weight average molecular weight ($M_w$) and the performance of the product as a drilling fluid additive.

In order to attain high $M_w$ values it is necessary to carry out dehydration as far as possible. By dehydration under gradually decreasing pressure it is possible to achieve a degree of dehydration which approaches and exceeds 1 mole of water per mole of glycerol. At this point, theoretically the glycerol feed could have polymerized to yield a single molecule of infinitely high molecular weight. However, in the course of distillation of glycerol from a basic medium, extensive cyclization takes place, which yields compounds such as cis- or trans-2,5-bis(hydroxymethyl)-p-dioxane, cis- or trans-2,6-bis(hydroxymethyl)-p-dioxane and the glycerine acetal of hydracrylaldehyde, or other 5-, 6-, or 7-membered ring structures of which the first two are predominant. The polycondensation of such cyclic structures with linear or branched polylglycerols yields polyethercyclicpolyolso Excellent polyethercyclicpolyols for drilling fluid applications can be obtained by dehydrating to the extent of 1.15 to 1.2 moles of water per mole of glycerol in the product.

Polyethercyclicpolyols are characterized by the presence of at least one and usually more than one 5- to 7-membered ring structures per individual molecule in at least 80 percent of the molecular mass. Moreover, a minimum of 20 percent, preferably 30 percent, and most preferably 40 percent, of all molecules of reactant participating on the formation of polyethercyclicpolyols are involved in cyclic structures.

The preferred way to achieve such extensive dehydration without undesirable degeneration and gelation of polyethercyclicpolyols is by the addition of small amounts of polyol, e.g., glycerol, at a later stage of the reaction, for example, when the reaction medium temperature has reached 270° to 280° C. at a pressure of 50 to 100 mm Hg, preferably 60 to 90 mm Hg. At least 3 percent by weight of polyol should be added to that effect, although more typically larger aliquots are added not once but several times. Upon addition of 2 to 6 percent by weight of polyol, e.g. glycerol, (basis final weight of polyol added) at a point after removal, for example, of 0.8 moles of water per mole of polyol, a drop in the temperature of the reacting mixture occurs, the drop being several degrees Centigrade or Fahrenheit. The drop is caused by the lower temperature of the polyol being added, but more importantly indicates the endothermic nature of the reaction between polyol molecules, or preferably between added polyol molecules and reactive sites in the prepolymerized mixture. For better effectiveness, the added polyol, e.g., glycerol, may be presaturated with alkali metal hydroxide, e.g., sodium hydroxide. In general the stepwise addition of glycerol should be initiated when the reaction is at least 40 percent complete (basis the amount of reactant present at the end of the reaction).

Upon continued input of heat from an external source, the temperature of the reacting mixtures rises to the previous highest level, or to a higher level, or to a somewhat lower level than the first high temperature, depending upon the molecular weight distribution of polyethercyclicpolyols in the mixture. This results in at least some of the polymerized polyol compounds achieving higher and higher molecular weights. Since the $M_w$ values are very sensitive to the presence of even small amounts of large molecules, this procedure results in increasing $M_w$ values which, generally results in improved performance in drilling mud formulations. This procedure of incremental polyol addition can be repeated any number of times, three being a convenient number. With three additions of polyol the experimental reaction time usually takes 6.5 to 7 hours and when optimally performed, excellent polyethercyclicpolyols are obtained.

The final $M_w$ values obtained are a strong function of the maximum temperature used in the polymerization reaction. Typical maximum temperatures range from 2500° C. to 295° C. at a pressure 40 to 80 mm Hg, preferably 270° C. to 295° C., and most preferably 275° C. to 285° C.

As the reaction approaches 85 percent completion, it is suitable to combine polyol additions with further reductions of pressure, going down to 30 mm Hg, or even lower. This results in deeper dehydration at a given temperature and therefore in higher $M_w$ and $M_n$ values.

Termination of Reaction

As the reaction of the present invention approaches completion, it turns from being highly endothermic to being more thermally neutral, and at a dehydration approaching and exceeding 1.2 moles of water per mole of polyol it can become exothermic. This is a reflection of the propensity of the mixture to undergo rapid degeneration of the complex polyethercyclicpolyol structures. In order to avoid the occurrence of such an undesirable degeneration, it is preferred to buffer the reaction by adding a small amount of monomeric polyol such as glycerol, for example, 0.2 to 2 percent, and preferably 0.3 to 0.9 percent by weight total. Preferably, there is added 0.5 percent by weight of polyol at a selected time such as when the reaction is at least 90 percent complete, or preferably at a point where the reaction is 95 percent complete, i.e., after removal of 1.12 to 1.15 moles of water per mole of polyol in the reaction medium. After reaction is terminated the polyethercyclicpolyol is removed from the reaction kettle, preferably by dilution with at least 20 percent weight water.

Dehydration in Relation to Feed Composition

With glycerol as the primary reaction medium, it is preferable to remove at least 1.05 and more preferably at least approximately 1.12 moles of water per mole of glycerol. Most preferably 1.15 to 1.25 moles of water per mole of glycerol in the product should be removed. If the feed contains an appreciable amount of predehydrated glycerol polymers, then the remaining dehydration will be less than 1.2 moles per mole of glycerol. As an example, for a known commercial product which typically contains 15 percent by weight of bis(hydroxymethyl)-dioxanes, and 85 percent by weight of glycerol the dehydration can be calculated as follows. For approximately 100 grams of feed there are 85 grams of glycerol (0.99 moles) and 15 grams of bis(hydroxymethyl)-dioxane (0.1014 moles). The glycerol component will have to lose $0.92 \times 1.2 = 1.104$ moles of water. The 0.1014 moles of bis(hydroxymethyl)-dioxane is derived from 0.2028 moles of glycerol by removal of 0.2028 moles of water; 1.2 total moles water per mole of glycerol should be removed, i.e., $0.2028 \times 1.2 = 0.2434$ moles. Thus it is necessary to remove $0.2434 - 0.22028 = 0.0406$ moles of water. The total to be removed is 1.104 moles from the glycerol $+ 0.0406$ moles from the bis(hydroxymethyl)-dioxane $= 1.1496$ moles water (or approximately 1.145 moles) from the 100 grams of the known commercial product.

Therefore it is necessary to remove close to 1.2 moles of water for each mole of glycerol which enters into the condensation of an initially partially dehydrated glycerol feed stream. Alternatively, in most cases involving complex feed streams, it would be appropriate to carry out the reaction and select a final maximum reaction temperature at set pressure conditions, such as is known from previous experience to yield satisfactory polyethercyclicpolyol preparations.

Part of the metal halide salt byproduct may also be removed by precipitation through the addition of a lower alkanol, such as n-propanol, methanol, n-butanol or n-pentanol. As the average molecular weight of the polyethercyclicpolyol samples increases, however, this salt extraction becomes less feasible; much of the product may precipitate with the solid salt.

The sample is typically diluted with water to 50 percent by weight for use as a drilling fluid additive. The sample may be analyzed for $Cl^-$ content. FAB-MS may be used to evaluate cyclic components (vide infra). $^{13}C$ NMR may also provide evidence of cyclicity (vide infra). Liquid and/or gas chromatography may be used to analyze light ends.

Characterization and Analysis

Figure 1A:
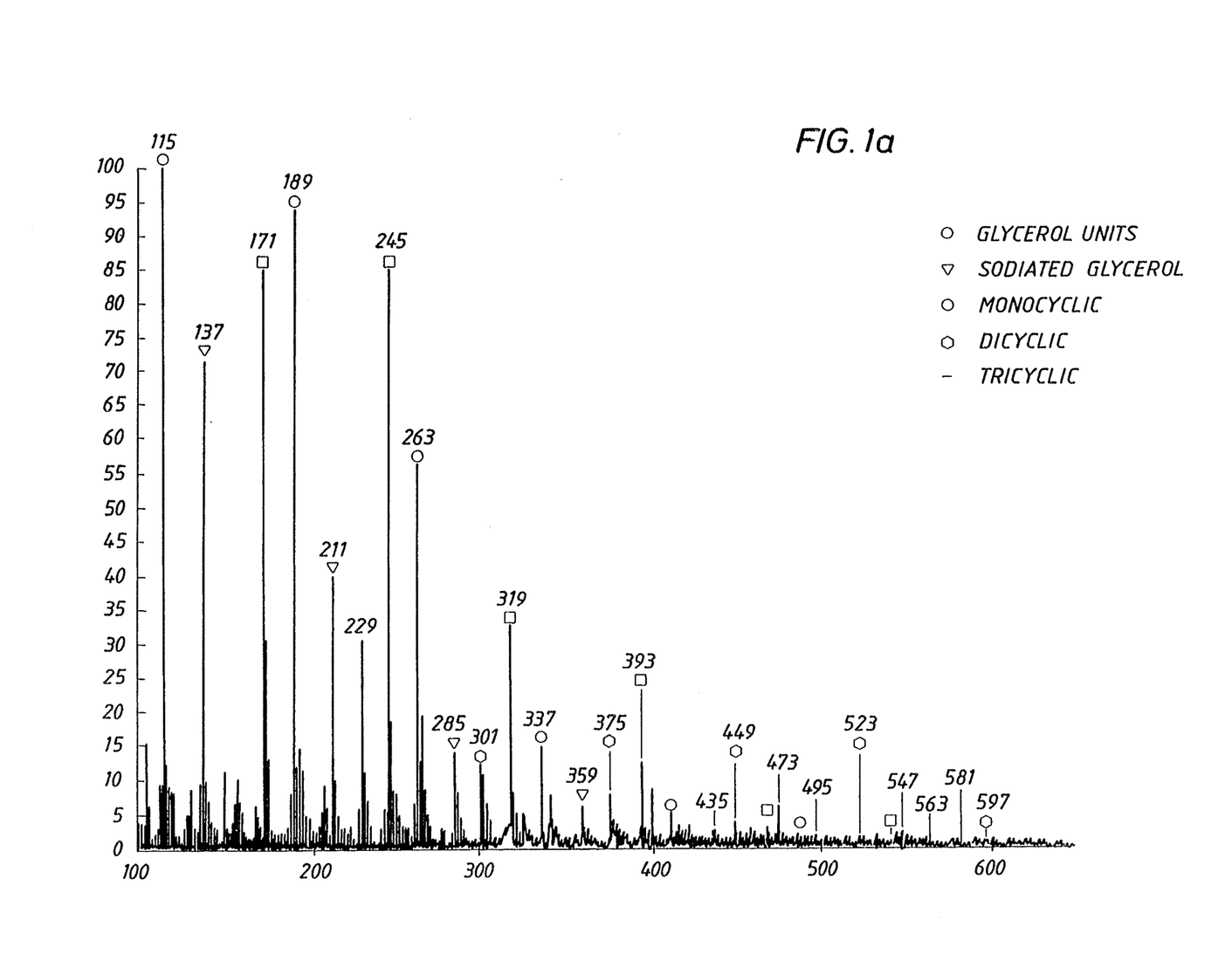
FIGS. 1A–1C disclose fast atom bombardment mass spectrometry for various samples.
Figure 1B:
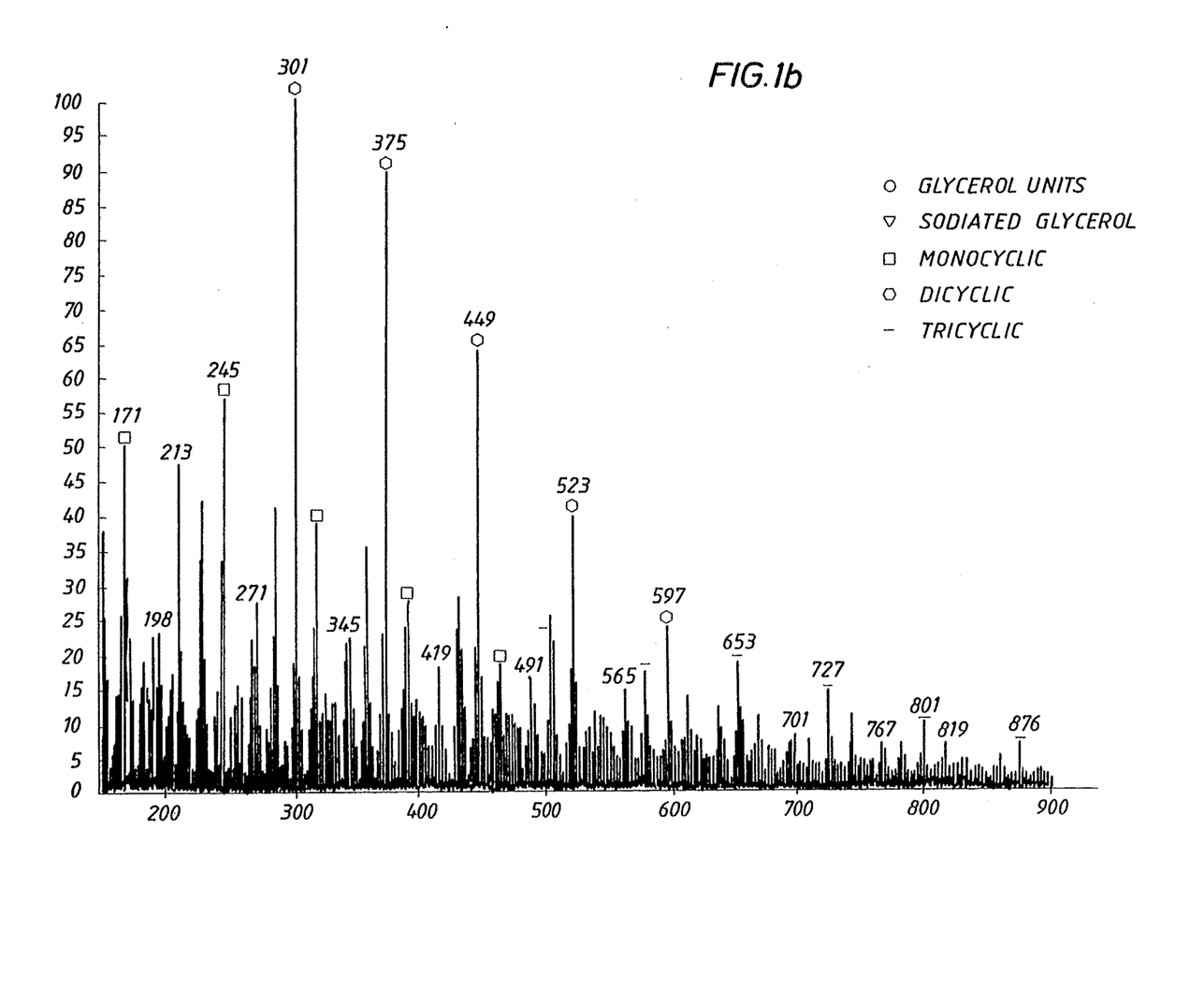
Figure 1C:
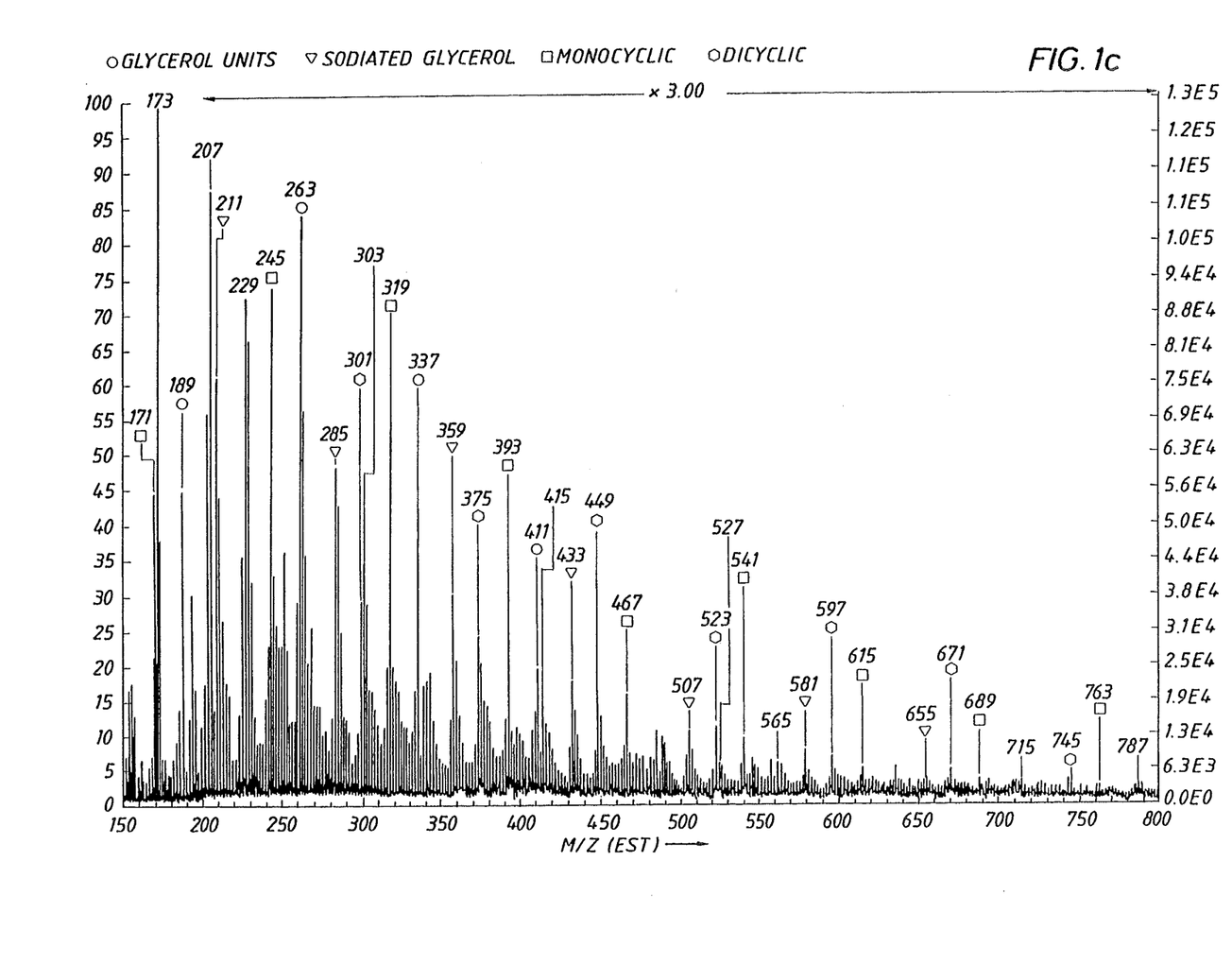

Fast atom bombardment mass spectrometry (FAB-MS) and C-13 nuclear magnetic resonance spectroscopy (NMR) techniques have been used to characterize polyethercyclicpolyol samples. FIG. 1 shows a comparison of the fast atom bombardment mass spectra of a) a concentrate of an aqueous effluent stream containing glycerol and its precursors, b) a polyethercyclicpolyol prepared via the thermal polycondensation of the glycerol concentrate described in a), as disclosed in the earlier patent application Ser. No. 672,200 filed Mar. 19, 1991, and c) a polyethercyclicpolyol prepared via the addition of epichlorohydrin and glycerol in the presence of sodium hydroxide, followed by a thermal condensation reaction, as described in Example 1 (vide supra).

The glycerol concentrate in FIG. 1A shows prominent ions at m/z 115 and 137, corresponding to the ionization of glycerol via attachment of one and two sodium atoms, respectively. Therefore, ionization via sodium adduction is expected for the hydroxyl-containing components in the samples. A series of masses m/z 189, 263, 337, etc. (symbolized by o) is also observed. Each member of this series is separated by 74 mass units, consistent with the addition of one glycerol unit (molecular weight 92) with the expulsion of one molecule of water (molecular weight 18). The molecular weights of the sodiated ions in this series are consistent with the (linear) condensation products of glycerol. In the presence of sodium, it is common to observe the replacement of acidic hydrogens with sodium, thus increasing the mass of the ion by 22. This series is represented in FIG. 1A by the symbol ∇.

Note that the above series of ions, o and ∇, are not abundant in the polyethercyclicpolyol sample in FIG. 1B. However, a loss of water from the condensation product of glycerol results in the series represented by ▯. It is expected that with the additional loss of one molecule of water, the glycerol dimer will form the six-membered ring diether structure, bis(hydroxymethyl)-p-dioxane. This series, based on the monocyclic dimer was observed in both the glycerol concentrate (FIG. 1A) and the polyethercylicpolyol samples (FIGS. 1B and 1C).

The condensation of four glycerol units, producing a 12-carbon-containing oligomer, presents the first opportunity for the formation of a dicyclic compound, through yet another loss of water. The series represented by and beginning at m/z 301 is consistent with the expulsion of water from the monocyclic tetramet at m/z 319 to produce the dicyclic tetramer. This series, based on the dicyclic tetramer, was observed in all the samples, however, the dicylic species dominate the spectrum of the polyethercyclicpolyol in FIG. 1B and are abundant in the spectrum of FIG. 1C.

The opportunity to increase the number of 6-membered rings in the polymer chain presents itself with each addition of two glycerol units, that is six carbons. Therefore, the dicyclic hexamer of glycerol (18 carbons, m/z 449) would form the tricyclic hexamer m/z 431, with the loss of water. The series of ions indicating the presence of the tricyclic hexamer does not appear in the spectrum of the glycerol concentrate in FIG. 1A, yet this higher mass series, symbolized by —, indicating the tricyclic hexamer is prominent in the polyethercyclicpolyol sample in FIG. 1B. This series of ions does not appear in the polyethercyclicpolyol sample in FIG. 1C.

The high molecular weight series of ions beginning with the tricyclic hexamer is observed for as many as 12 glycerol units, m/z 876, however detection limitations cause higher mass components to become increasingly more difficult to ionize and detect by this method.

Therefore, it may be seen from the FAB-MS spectra that the aqueous effluent stream concentrate (shown in FIG. 1A) contains some cyclic glycerol-derived products along with linear polyglycerols, however, the polyethercyclicpolyols represented in FIGS. 1B) and 1C), prepared by the thermal condensation of polyols and by the additions of epihalohydrins and polyols followed by thermal condensation as described herein, respectively, show that the linear polyglycerol is not abundant and the sample consists mostly of the cyclic glycerol-derived products.

C-13 NMR analysis of the polyethercyclicpolyol samples dissolved in methanol or $D_2O$/methanol are shown in FIG. 2. FIG. 2 shows a comparison of the C-13 NMR spectra of a) a polyethercyclicpolyol prepared via the thermal polycondensation of the glycerol concentrate described above, as disclosed in the earlier patent application Ser. No. 672,200 filed Mar. 19, 1991, and b) a polyethercyclicpolyol prepared via the addition of epichlorohydrin and glycerol in the presence of sodium hydroxide, followed by the thermal condensation reaction. The NMR spectra show similar chemical structure and are consistent with the structures proposed for these samples. The components of interest occur in the C-13 NMR spectrum between 90 and 55 ppm chemical shift. This part of the spectrum can be broken down into three regions:

90–76 ppm: Branch point/cyclization point carbons RR'CH—OR"

76–65 ppm: Internal linear carbons —$CH_2$—OR

65–55 ppm: Linear terminal carbons —$CH_2$—OH

The integrals of the peaks in these three regions of the C-13 NMR spectrum for the samples shown in FIG. 2 are summarized in Table 1.

TABLE 1

Figure 2A:
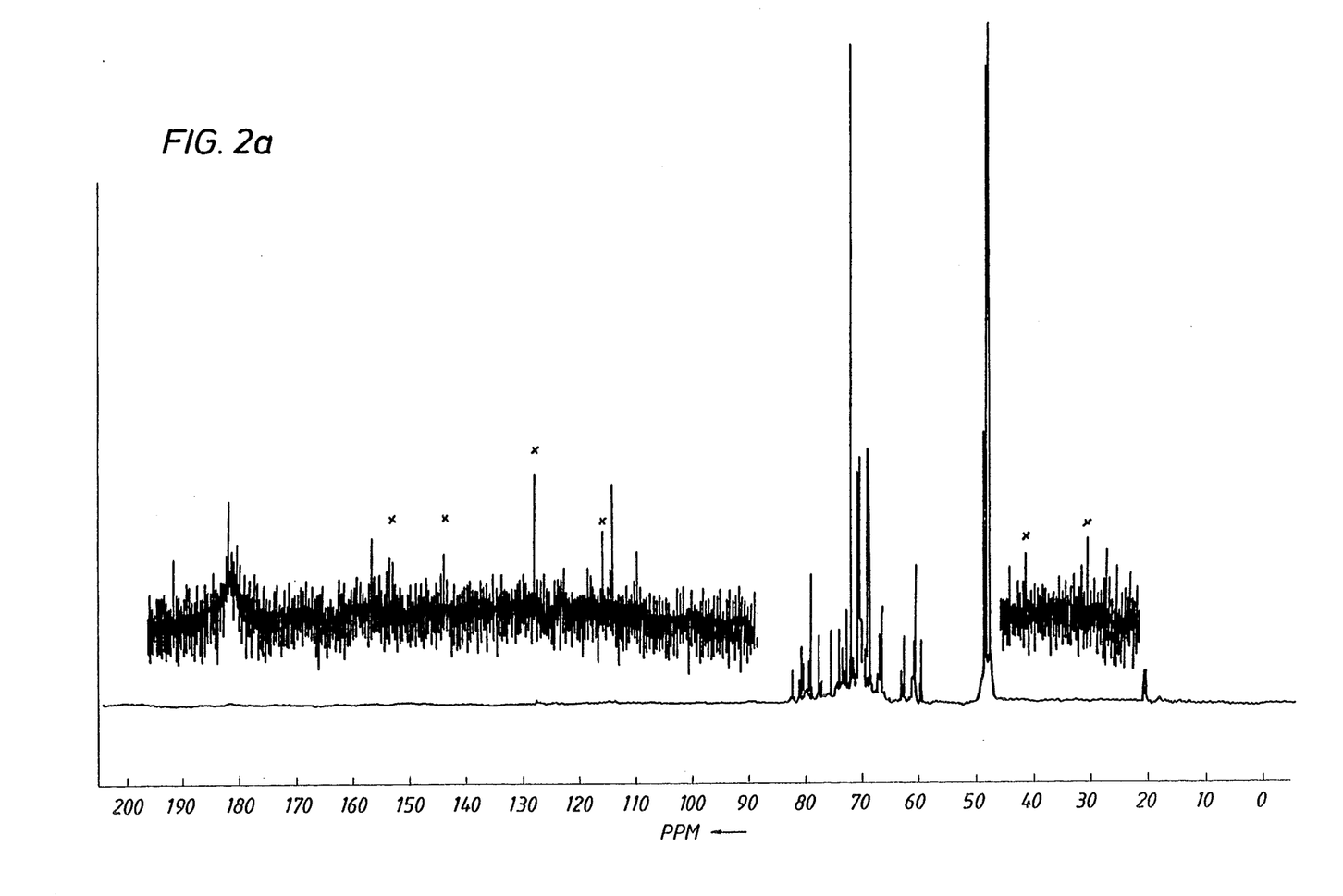
FIGS. 2A and 2B disclose nuclear magnetic resonance spectroscopy for various samples.
Figure 2B:
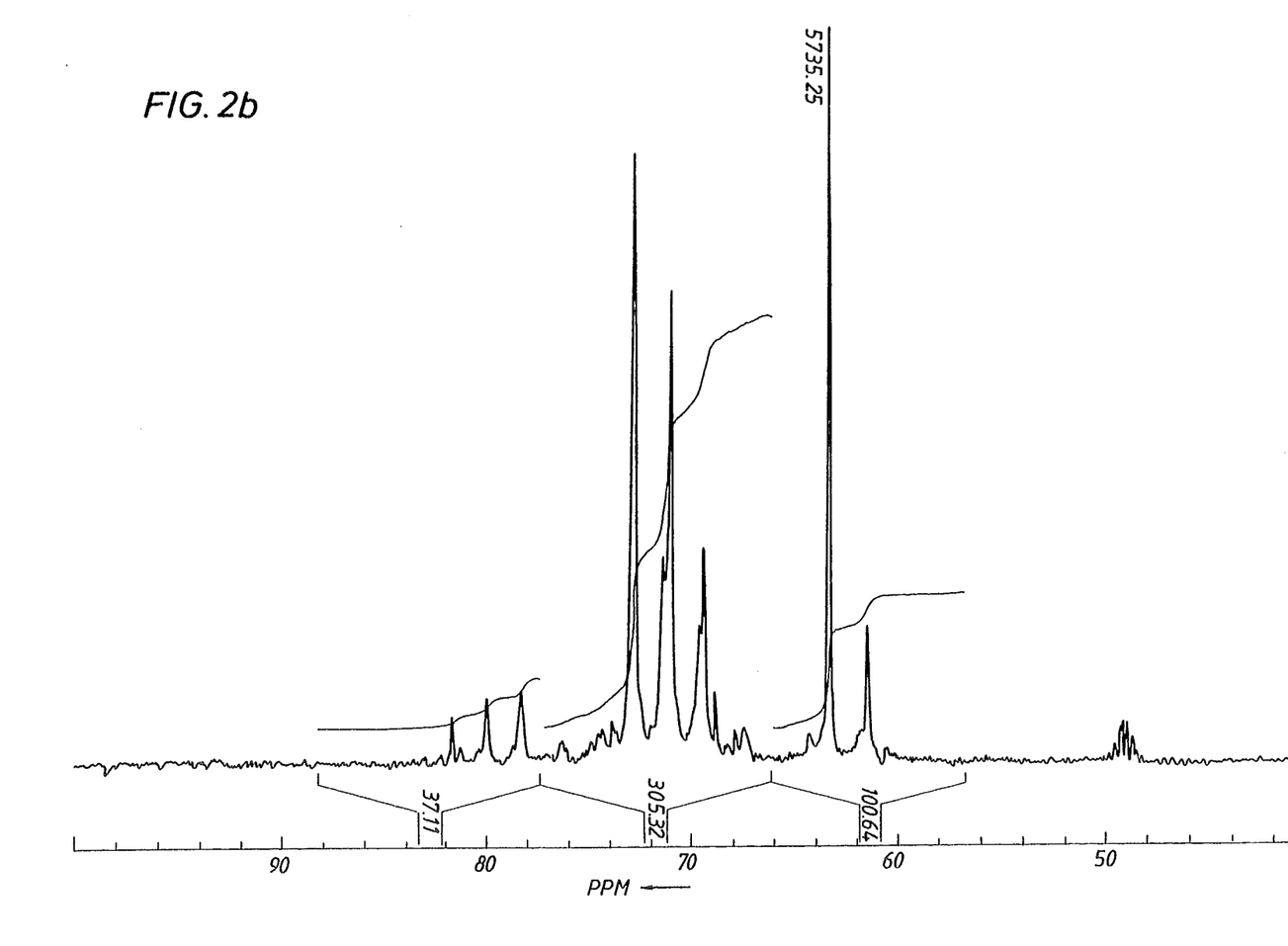

| Sample | 90–76 ppm Integral | 76–66 ppm Integral | 66–55 ppm Integral | Sum | Polymerized C3 | |
|---|---|---|---|---|---|---|
| | | | | | Branches Per 100 | End Per 100 |
| FIG. 2a | 20 | 103.5 | 15 | 138.5 | 43 | 32 |
| FIG. 2b | 37 | 305 | 101 | 443 | 25 | 68 |

Since the polyethercyclicpolyol is of an unknown high molecular weight, the integrals of the three regions cannot be used to differentiate between an average molecular structure and an average repeat unit structure. What can be stated, however, is that for the polyethercyclicpolyol sample prepared via thermal polycondensation (FIG. 2A), the branch point/cyclization point carbons outnumber the terminal carbons. Such a situation cannot be reconciled with a structure that is simply branched and therefore the structure must be at least partially cyclized. The C-13 spectrum of the sample prepared via addition of epichlorohydrin and glycerol (FIG. 2B) is similar to the thermally prepared sample, but has lower cyclicity.

Since the FAB-MS profiles shown in FIGS. 1B) and 1C) are similar, showing the presence of both monocyclic and dicyclic species in FIG. 1C), we conclude that polyethercyclicpolyols may be produced by the method of the present invention described herein. This conclusion is further supported by the C-13 NMR data.

EXAMPLES

Example 1a

Preparation of Polyethercyclicpolyol Via Addition of Epichlorohydrin and Glycerol in the Presence of Sodium Hydroxide Employing Acetone as the Solvent 204 g glycerol (2.21 moles), 128 g granular solid sodium hydroxide (3.20 moles), and 350 ml acetone were charged to a 500 ml resin kettle fitted with a thermocouple, a nitrogen inlet, a metering addition funnel, an air-driven stirrer and a 1-inch diameter, 15-inch high Vigreaux column (equivalent to ca. 10 plates) attached to a vacuum distillation head which allows complete or partial takeoff of reflux with a condenser cooled with chilled (11° C.) water. The top of the resin kettle and the Vigreaux column were insulated. A nitrogen flow of 1.5 standard cubic feet per hour (SCFH) was begun. A heating mantle was used to heat the kettle. The mixture was heated to 59° C. and this temperature was held for 5 minutes. After 3 minutes, the nitrogen flow was reduced to 1SCFH. 172 ml epichlorohydrin (203 g, 2.20 moles) was then added dropwise from the addition funnel over a period of 90 minutes, for an average addition rate of 1.9 ml/min. The reaction temperature was maintained between 59° C. and 69° C., during which time the mixture refluxed. All reflux was returned to the reaction mixture. Water (35 ml) was added to the mixture 35 minutes after the epichlorohydrin addition was begun. Heating was continued for 45 minutes after the epichlorohydrin addition was complete. The solvent was removed by distillation at atmospheric pressure. At this point, 223 g of glycerol (2.42 moles) and 51.5 ml (61.8 g, 0.627 moles) of 37% weight aqueous hydrochloric acid was added to the mixture. Distillation at atmospheric pressure was continued under the mixture temperature had risen to 100° C. and about 220 ml distillate had been collected.

Example 1b

Preparation of Polyethercyclicpolyol Via Thermal Co-Polycondensation of Low Average Molecular Weight Polyethercyclicpolyol, Glycerol and Diglycidyl Ether in the Presence of Sodium Hydroxide, with Glycerol Added at Later Stages To the apparatus containing the final mixture described in Example 1a were attached two receivers containing 100 ml sodium hydroxide-saturated glycerol (126 g, 1.37 moles) and 21 ml liquid "EPON 828" epoxy resin, a difunctional diglycidyl ether, respectively. Distillation under reduced pressure was begun at 86° C. and 300 mm Hg pressure. A 1:1 reflux ratio was used to continuously remove a water-rich overhead, minimizing the loss of glycerol, as the polycondensation reaction proceeded. The pressure was adjusted to 40 mm Hg. As a result the mixture temperature was reduced to 73° C. 26 ml overhead was obtained. The pressure was then increased to 160 mm Hg and the temperature of the mixture allowed to rise to 127° C. At this point, 7 ml "EPON 828" was added to the mixture. The reaction continued to a boiling point of 224° C. at 160 mm Hg, at which point an additional 38 ml overhead had collected. The pressure was adjusted to 100 mm Hg, at a mixture boiling temperature of 233° C. An additional 7 ml "EPON 828" was added to the mixture. The temperature in the kettle was allowed to rise to 246° C. At this point the pressure was reduced to 80 mm Hg, and 30 ml sodium hydroxide-saturated glycerol was added to the mixture. At 225° C., the pressure was reduced to 50 mm Hg. As a result the mixture boiling temperature was reduced to 221° C. The temperature was allowed to rise to 230° C. At this time, an additional 50 ml overhead had collected. An additional 40 ml sodium hydroxide-saturated glycerol was added to the mixture. When the mixture temperature climbed to 238° C., the pressure had to be increased to 100 mm Hg to keep the material inside the flask. The temperature correspondingly dropped to 222° C. and an additional 30 ml sodium hydroxide-saturated glycerol was added. The pressure was increased further to 120 mm Hg. The mixture was a bright yellow color, and the material climbed the stirring shaft. The reaction temperature climbed to 243° C. at 125 mm Hg. An additional 40 ml overhead had collected. The mixture color had darkened to a deep brown. The reaction was stopped. A total of 140 ml overhead was removed in the reaction. The cooled reaction mixture was diluted with water to 50 percent aqueous. The material was tested as a drilling fluid additive.

Example 2a

Preparation of Polyethercyclicpolyol Via Addition of Epichlorohydrin and Glycerol in the Presence of Sodium Hydroxide Employing Acetone as the Solvent 204 g glycerol (2.21 moles), 128 g granular solid sodium hydroxide (3.20 moles), and 350 ml acetone were charged to the apparatus described in Example 1a. A nitrogen flow of 1.5 standard cubic feet per hour (SCFH) was begun. The mixture was heated from 59° C. to 64° C. over 5 minutes. 172 ml epichlorohydrin (203 g, 2.20 moles) was then added dropwise from the addition funnel over a period of 82 minutes, for an average addition rate of 2.0 ml/min. The reaction temperature was maintained between 59° C. and 67° C., during which time the mixture refluxed. All reflux was returned to the reaction mixture. No water was added to the reaction mixture. Heating was continued for 85 minutes after the epichlorohydrin addition was complete. The solvent was removed by distillation at atmospheric pressure. The mixture climbed the stirring shaft. At this point, 219 g of glycerol (2.38 moles) was added to the mixture and solvent removal was continued. When no more solvent was removed (238 ml overhead was collected), 51.5 ml (61.8 g, 0.627 moles) of 37% weight aqueous hydrochloric acid was added to the mixture.

Example 2b

Preparation of Polyethercyclicpolyol Via Thermal Co-Polycondensation of Low Average Molecular Weight Polyethercyclicpolyol, Glycerol and Diglycidyl Ether in The Presence of Sodium Hydroxide, with Glycerol Added at Later Stages To the apparatus containing the final mixture described in Example 2a were attached two receivers containing 100 ml sodium hydroxide-saturated glycerol (126 g, 1.37 moles) and 21 ml liquid "EPON 828" epoxy resin, a difunctional diglycidyl ether, respectively. The mixture was heated to 98° C. The pressure was reduced to 265 mm Hg. At 93° C., liquid began to distill. The pressure was slowly reduced to 180 mm Hg. The temperature rose to 99° C. at 180 mm Hg, and 35.5 ml overhead had collected. At this point, 7 ml "EPON 828" was added to the mixture. A 1:1 reflux ratio was established to continuously remove a water-rich overhead, minimizing the loss of glycerol, as the polycondensation reaction proceeded. The mixture temperature was allowed to rise to 142° C. At this point, 27.5 additional overhead had been removed, and 7 ml additional "EPON 828" was added to the mixture. The reaction continued to a boiling point of 210° C. at 180 mm Hg, at which point an additional 10 ml "EPON 828" was added. The temperature was allowed to rise to 2300° C., and the pressure was adjusted to 100 mm Hg, causing the mixture temperature to decrease to 2250° C. The temperature was allowed to rise to 231° C., and the pressure was adjusted to 80 mm Hg. At this point 35 ml sodium hydroxide-saturated glycerol was added to the mixture. The temperature in the kettle was allowed to rise to 224° C. At this point the pressure was reduced to 60 mm Hg. 35 ml sodium hydroxide-saturated glycerol was added to the mixture shortly after. The temperature was allowed to rise to 247° C., at which point the reaction mixture was bright yellow in color. An additional 30 ml glycerol was added to the mixture. When the temperature rose to 257° C., the pressure was slowly decreased to 30 mm Hg. The temperature rose to 2750° C., and the reaction was stopped. An additional 83 ml overhead had collected for a total of 146 ml overhead removed. The mixture color had darkened to a light caramel. The cooled reaction mixture was diluted with water to 50 percent aqueous. The material was tested as a drilling fluid additive.

What is claimed is:

1. A product prepared by a method for preparing polyetherpolycyclicpolyol, comprising:
    a) at a pressure of 150 to 300 mm Hg and a temperature that rises to 210° C. to 230° C., reacting an epoxy alcohol in the presence of sodium hydroxide catalyst in a concentration of 0.5 to 1.5 percent by weight of the reaction mixture by slowly adding the epoxy alcohol to the catalyst while heating to form a first mixture having a starting pH ranging from 5 to 13.5;
    b) continuing heating the first mixture until the reaction is substantially complete and pH has declined to 5 to 9.5 and temperature has risen to 250° to 295° C. at a pressure of 40 to 80 mm HG;
    c) optionally adding polyol reactant selected from the group consisting of (1) a polyol having at least two hydroxyl groups, (2) precursors of the polyol, (3) cyclic derivatives of the polyol, and (4) mixtures thereof, to the first mixture to form a second mixture;
    d) heating the second mixture to initiate thermal condensation, and removing water formed during the thermal condensation;
    e) optionally adding a final quantity of the polyol reactant; and
    f) continuing the thermal condensation substantially to completion.

2. The product prepared by the method of claim 1 wherein the metal hydroxide is admixed with a solvent and heated prior to adding the epoxy alcohol.

* * * * *